(12) United States Patent
Scirica et al.

(10) Patent No.: US 7,780,055 B2
(45) Date of Patent: Aug. 24, 2010

(54) LOADING UNIT HAVING DRIVE ASSEMBLY LOCKING MECHANISM

(75) Inventors: Paul A. Scirica, Huntington, CT (US); Roman Czernik, Trumbull, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 1509 days.

(21) Appl. No.: 11/100,279

(22) Filed: Apr. 6, 2005

(65) Prior Publication Data
US 2006/0226195 A1 Oct. 12, 2006

(51) Int. Cl.
*A61B 17/10* (2006.01)

(52) U.S. Cl. ............ 227/175.2; 227/175.1; 227/175.3; 227/181.1; 227/19

(58) Field of Classification Search .............. 227/19, 227/175.1–175.3, 181.1
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 4,429,695 A | 2/1984 | Green | |
| 4,505,414 A | 3/1985 | Filipi | |
| 4,589,413 A | 5/1986 | Malyshev et al. | |
| 4,602,634 A | 7/1986 | Barkley | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |
| 4,703,887 A | 11/1987 | Clanton et al. | |
| 4,728,020 A | 3/1988 | Green et al. | |
| 4,752,024 A | 6/1988 | Green et al. | |
| 4,784,137 A | 11/1988 | Kulik et al. | |
| 4,863,088 A | 9/1989 | Redmond et al. | |
| 4,892,244 A | 1/1990 | Fox et al. | |
| 4,978,049 A | 12/1990 | Green | |
| 4,991,764 A | 2/1991 | Mericle | |
| 5,040,715 A | 8/1991 | Green et al. | |
| 5,065,929 A | 11/1991 | Schulze et al. | |
| 5,074,454 A | 12/1991 | Peters | |
| 5,083,695 A | 1/1992 | Foslien et al. | |
| 5,084,057 A | 1/1992 | Green et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |

(Continued)

FOREIGN PATENT DOCUMENTS

DE 2744824 4/1978

(Continued)

*Primary Examiner*—Rinaldi I. Rada
*Assistant Examiner*—Michelle Lopez (57) ABSTRACT

A disposable loading unit is provided which includes a tool assembly and a body portion. A drive assembly is movably positioned at least partly within the body portion and is operably associated with the tool assembly to operate the tool assembly. A locking mechanism is provided for maintaining the drive assembly in a prefired position prior to and during attachment of a DLU to a surgical instrument. The locking mechanism includes a locking member and a locking member actuator. The locking member actuator is movable to move the locking member to an unlocked position in response to linear insertion of an insertion tip of the DLU into a surgical instrument.

4 Claims, 11 Drawing Sheets

U.S. PATENT DOCUMENTS

| | | |
|---|---|---|
| 5,170,925 A | 12/1992 | Madden et al. |
| 5,246,156 A | 9/1993 | Rothfuss et al. |
| RE34,519 E | 1/1994 | Fox et al. |
| 5,282,807 A | 2/1994 | Knoepfler |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,332,142 A | 7/1994 | Robinson et al. |
| 5,336,232 A | 8/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,376,095 A | 12/1994 | Ortiz |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,573,543 A | 11/1996 | Akopov et al. |
| 5,575,799 A | 11/1996 | Bolanos et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,704,534 A | 1/1998 | Huitema et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,725,536 A | 3/1998 | Oberlin et al. |
| 5,725,554 A | 3/1998 | Simon et al. |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A * | 9/1998 | Robertson et al. ........ 227/179.1 |

| | | | | | | |
|---|---|---|---|---|---|---|
| 5,810,811 | A | 9/1998 | Yates et al. | 6,889,116 B2 | 5/2005 | Jinno |
| 5,810,855 | A | 9/1998 | Rayburn et al. | 6,905,057 B2 | 6/2005 | Swayze et al. |
| 5,814,055 | A | 9/1998 | Knodel et al. | 2002/0004498 A1 | 1/2002 | Doherty |
| 5,816,471 | A | 10/1998 | Plyley et al. | 2002/0009193 A1 | 1/2002 | Deguchi |
| 5,817,109 | A | 10/1998 | McGarry et al. | 2002/0018323 A1 | 2/2002 | Li |
| 5,820,009 | A | 10/1998 | Melling et al. | 2002/0032948 A1 | 3/2002 | Ahn |
| 5,823,066 | A | 10/1998 | Huitema et al. | 2002/0036748 A1 | 3/2002 | Chapoy |
| 5,826,776 | A | 10/1998 | Schulze et al. | 2002/0045442 A1 | 4/2002 | Silen et al. |
| 5,829,662 | A | 11/1998 | Allen et al. | 2002/0069595 A1 | 6/2002 | Liao |
| 5,833,695 | A | 11/1998 | Yoon | 2002/0084304 A1 | 7/2002 | Whitman |
| 5,836,147 | A | 11/1998 | Schnipke | 2002/0111621 A1 | 8/2002 | Wallace |
| 5,862,972 | A | 1/1999 | Green et al. | 2002/0143346 A1 | 10/2002 | McGuckin |
| 5,865,361 | A | 2/1999 | Milliman et al. | 2002/0177843 A1 | 11/2002 | Anderson |
| 5,871,135 | A | 2/1999 | Williamson, IV et al. | 2002/0188294 A1 | 12/2002 | Couture |
| 5,873,873 | A | 2/1999 | Smith et al. | 2002/0190093 A1 | 12/2002 | Fenton |
| 5,897,562 | A | 4/1999 | Bolanos et al. | 2003/0009193 A1 | 1/2003 | Corsaro |
| 5,901,895 | A | 5/1999 | Heaton et al. | 2003/0105476 A1 | 6/2003 | Sancoff |
| 5,911,353 | A | 6/1999 | Bolanos et al. | 2003/0132268 A1 | 7/2003 | Whitman |
| 5,918,791 | A | 7/1999 | Sorrentino et al. | 2004/0004105 A1 | 1/2004 | Jankowski |
| 5,919,198 | A | 7/1999 | Graves, Jr. et al. | 2004/0007608 A1 | 1/2004 | Ehrenfels |
| 5,922,001 | A | 7/1999 | Yoon | 2004/0050902 A1 | 3/2004 | Green |
| 5,954,259 | A | 9/1999 | Viola et al. | 2004/0093029 A1 | 5/2004 | Zubik |
| 5,980,510 | A | 11/1999 | Tsonton et al. | 2004/0094597 A1 | 5/2004 | Whitman |
| 6,004,335 | A | 12/1999 | Vaitekunas et al. | 2004/0108357 A1 | 6/2004 | Milliman |
| 6,010,054 | A | 1/2000 | Johnson et al. | 2004/0149802 A1 | 8/2004 | Whitman |
| 6,032,849 | A | 3/2000 | Mastri et al. | 2004/0173659 A1 | 9/2004 | Green |
| 6,079,606 | A | 6/2000 | Milliman et al. | 2004/0199181 A1 | 10/2004 | Knodel |
| 6,109,500 | A | 8/2000 | Alli et al. | 2004/0232199 A1 | 11/2004 | Shelton |
| 6,197,017 | B1 | 3/2001 | Brock et al. | 2004/0232200 A1 | 11/2004 | Shelton |
| 6,202,914 | B1 | 3/2001 | Geiste et al. | 2004/0232201 A1 | 11/2004 | Wenchell |
| 6,241,139 | B1 | 6/2001 | Milliman et al. | 2004/0243151 A1 | 12/2004 | Demmy |
| 6,250,532 | B1 | 6/2001 | Green et al. | 2004/0267310 A1 | 12/2004 | Racenet |
| 6,264,086 | B1 | 7/2001 | McGuckin, Jr. | 2005/0006429 A1 | 1/2005 | Wales |
| 6,264,087 | B1 | 7/2001 | Whitman | 2005/0006430 A1 | 1/2005 | Wales |
| 6,269,977 | B1 | 8/2001 | Moore | 2005/0006431 A1 | 1/2005 | Shelton |
| 6,279,809 | B1 | 8/2001 | Nicolo | 2005/0006432 A1 | 1/2005 | Racenet |
| 6,315,183 | B1 | 11/2001 | Piraka | 2005/0006433 A1 | 1/2005 | Milliman |
| 6,315,184 | B1 | 11/2001 | Whitman | 2005/0006434 A1 | 1/2005 | Wales |
| 6,325,810 | B1 | 12/2001 | Hamilton et al. | 2005/0023324 A1 | 2/2005 | Doll |
| 6,330,965 | B1 | 12/2001 | Milliman et al. | 2005/0023325 A1 | 2/2005 | Gresham |
| 6,436,097 | B1 | 8/2002 | Nardella | 2005/0067457 A1 | 3/2005 | Shelton |
| 6,439,446 | B1 | 8/2002 | Perry et al. | 2005/0067458 A1 | 3/2005 | Swayze |
| 6,443,973 | B1 | 9/2002 | Whitman | 2005/0067459 A1 | 3/2005 | Swayze et al. |
| 6,463,623 | B2 | 10/2002 | Ahn et al. | 2005/0067460 A1 | 3/2005 | Milliman |
| 6,488,196 | B1 | 12/2002 | Fenton, Jr. | 2005/0072827 A1 | 4/2005 | Mullenauer |
| 6,503,257 | B2 | 1/2003 | Grant et al. | 2005/0103819 A1 | 5/2005 | Racenet |
| 6,505,768 | B2 | 1/2003 | Whitman | 2005/0119669 A1 | 6/2005 | Demmy |
| 6,544,274 | B2 | 4/2003 | Danitz et al. | 2005/0127131 A1 | 6/2005 | Mastri |
| 6,554,844 | B2 | 4/2003 | Lee et al. | | | |
| 6,565,554 | B1 | 5/2003 | Niemeyer | | FOREIGN PATENT DOCUMENTS | |
| 6,587,750 | B2 | 7/2003 | Gerbi et al. | | | |
| 6,592,597 | B2 | 7/2003 | Grant et al. | DE | 2903159 | 1/1980 |
| 6,594,552 | B1 | 7/2003 | Nowlin et al. | DE | 4213426 | 10/1992 |
| 6,602,252 | B2 | 8/2003 | Mollenauer | DE | 4300307 | 7/1994 |
| 6,612,053 | B2 | 9/2003 | Liao | EP | 0041022 | 12/1981 |
| 6,619,529 | B2 | 9/2003 | Green et al. | EP | 0136950 | 4/1985 |
| 6,644,532 | B2 | 11/2003 | Green et al. | EP | 0140552 | 5/1985 |
| 6,656,193 | B2 | 12/2003 | Grant et al. | EP | 0156774 | 10/1985 |
| 6,669,073 | B2 | 12/2003 | Milliman et al. | EP | 0216532 | 4/1987 |
| 6,698,643 | B2 | 3/2004 | Whitman | EP | 0220029 | 4/1987 |
| 6,716,232 | B1 | 4/2004 | Vidal et al. | EP | 0213817 | 11/1987 |
| 6,722,552 | B2 | 4/2004 | Fenton, Jr. | EP | 0273468 | 7/1988 |
| 6,731,473 | B2 | 5/2004 | Li et al. | EP | 0324166 | 7/1989 |
| 6,755,338 | B2 | 6/2004 | Hahnen et al. | EP | 0324635 | 7/1989 |
| 6,783,524 | B2 | 8/2004 | Anderson et al. | EP | 0324637 | 7/1989 |
| 6,786,382 | B1 | 9/2004 | Hoffman | EP | 0324638 | 7/1989 |
| 6,808,262 | B2 | 10/2004 | Chapoy et al. | EP | 0369324 | 5/1990 |
| 6,830,174 | B2 | 12/2004 | Hillstead et al. | EP | 0373762 | 6/1990 |
| 6,835,119 | B2 | 12/2004 | Hori | EP | 0380025 | 8/1990 |
| 6,843,403 | B2 | 1/2005 | Whitman | EP | 0399701 | 11/1990 |
| RE38,708 | E | 3/2005 | Bolanos et al. | EP | 0449394 | 10/1991 |
| 6,877,647 | B2 | 4/2005 | Green et al. | EP | 0484677 | 5/1992 |
| 6,879,880 | B2 | 4/2005 | Nowlin et al. | EP | 0489436 | 6/1992 |

| | | | | | | |
|---|---|---|---|---|---|---|
| EP | 0503662 | 9/1992 | | EP | 0705571 | 4/1996 |
| EP | 0514139 | 11/1992 | | FR | 2542188 | 9/1984 |
| EP | 0536903 | 4/1993 | | FR | 2681775 | 10/1991 |
| EP | 0537572 | 4/1993 | | GB | 1352554 | 4/1971 |
| EP | 0539762 | 5/1993 | | GB | 1452185 | 10/1976 |
| EP | 0545029 | 6/1993 | | GB | 1555455 | 11/1979 |
| EP | 0552050 | 7/1993 | | GB | 2048685 | 12/1980 |
| EP | 0552423 | 7/1993 | | GB | 2070499 | 9/1981 |
| EP | 0579038 | 1/1994 | | GB | 2141066 | 12/1984 |
| EP | 0589306 | 3/1994 | | GB | 2165559 | 4/1986 |
| EP | 0591946 | 4/1994 | | SU | 728848 | 5/1977 |
| EP | 0592243 | 4/1994 | | SU | 659146 | 4/1979 |
| EP | 0593920 | 4/1994 | | SU | 980703 | 12/1982 |
| EP | 0598202 | 5/1994 | | SU | 990220 | 1/1983 |
| EP | 0598579 | 5/1994 | | WO | WO 89/10094 | 11/1989 |
| EP | 0621006 | 10/1994 | | WO | WO9210976 | 7/1992 |
| EP | 0621009 | 10/1994 | | WO | 9308754 | 5/1993 |
| EP | 0656188 | 6/1995 | | WO | WO8302247 | 7/1993 |
| EP | 0365153 | 8/1995 | | WO | 9314706 | 8/1993 |
| EP | 0666057 | 8/1995 | | | | |

* cited by examiner

LOADING UNIT HAVING DRIVE ASSEMBLY LOCKING MECHANISM

BACKGROUND

1. Technical Field

The present disclosure relates to a disposable loading unit ("DLU") or single use loading unit ("SULU") for use with a surgical device. More particularly, the present disclosure relates to a DLU or SULU for use with a surgical instrument which includes a locking mechanism for retaining a drive assembly of the loading unit in its prefired position until the loading unit is attached to a surgical device. For simplicity, hereinafter, SULU or DLU will be referred to as "DLU", but it should be understood to include either or both a DLU or SULU.

2. Background of Related Art

Surgical devices for applying fasteners, e.g., staples, clips, etc., to tissue are well known. Such devices include single use devices which are preloaded with a single fastener and are disposable after a single use of the device. Such devices also include multiple use devices which are preloaded with a plurality of fasteners and are disposable after the supply of fasteners has been exhausted or a surgical procedure has been completed. If the supply of fasteners is exhausted prior to completion of a surgical procedure, a new device may be required to complete the surgical procedure. The use of additional surgical devices for a single surgical procedure can be expensive.

In order to address the high expense of using multiple surgical devices for a single procedure, surgical devices having replaceable fastener cartridges have been developed. In such devices, fasteners are housed within a cartridge. When the fasteners in the cartridge have been exhausted, the cartridge can be removed from the surgical device and replaced with a new cartridge having an additional supply of fasteners.

Tyco Healthcare Group, LP, the assignee of the present application, has manufactured and marketed endoscopic stapling devices having replaceable cartridges, such as the Multifire ENDO GIA™ 30 and Multifire ENDO GIA™ 60 devices, for a number of years. These devices include a surgical stapling apparatus and a DLU. Typically, the DLU includes a proximal body portion and a distal tool member and is attached to a surgical apparatus immediately prior to surgery. The distal tool member includes a cartridge housing a plurality of staples. After use, the DLU can be removed from the apparatus and replaced with a new DLU to perform additional stapling and/or cutting operations. A drive assembly is supported within the DLU and is engageable with a control rod of the surgical apparatus to facilitate operation of the apparatus.

Although, these devices have provided significant clinical benefits, improvements to these devices are still possible. Accordingly, it would be desirable to provide an improved DLU for a surgical fastener applying device which retains or locks the DLU drive assembly in a prefired position until the DLU is attached to the surgical fastener applying device.

SUMMARY

In accordance with the present disclosure, a DLU is provided which includes a body portion and a tool assembly. A drive assembly is movably supported within the body portion from a retracted position to an advanced position. A locking member is supported on the body portion and is movable from a first position engaging the drive assembly to a second position disengaged from the drive assembly. A locking member actuator is operably engaged with the locking member to move the locking member from its first position to its second position when the DLU is inserted linearly into the distal end of a surgical instrument.

In one embodiment, the locking member includes a cam member which is slidably positioned within a cam slot formed in the locking member actuator. The locking member actuator is slidably positioned within a linear slot formed in the body portion and the locking member is slidably positioned within a transverse slot formed in the body portion. The locking member actuator includes an abutment member which is positioned on and extends radially outwardly from an insertion tip of the body portion. The abutment member is positioned to engage a surface on a surgical instrument when the body portion insertion tip is inserted into the distal end of a surgical instrument during attachment of the DLU to the surgical instrument. Engagement between the abutment member and the surgical instrument effects linear movement of the locking member actuator from a retracted position to an advanced position. Advancement of the locking member actuator is translated to transverse movement of the locking member from its first position to its second position via interaction between the cam member of the locking member and the cam slot of the locking member actuator.

In one embodiment, a biasing member, e.g., a spring, is provided to urge the locking member actuator to its retracted position. In the retracted position of the locking member actuator, the locking member is maintained in its first or locked position.

In one embodiment, the locking member includes a finger which is dimensioned to be received within a notch or recess formed in the drive assembly. In the first position of the locking member, the finger is positioned within the notch to prevent movement of the drive assembly from a retracted to an advanced position. Alternately, other engagement configurations are contemplated.

In one embodiment, the tool assembly includes a cartridge assembly and an anvil assembly which is movable in relation to the cartridge assembly between open and approximated positions. The tool assembly may include a linear cartridge assembly which includes a plurality of linear rows of staples, e.g., six. The tool assembly may also include knife blade which can be supported on a distal end of the drive assembly. The tool assembly may also be pivotally mounted to the body portion. Alternately, the presently disclosed locking mechanism may be incorporated into other surgical devices including staplers, clip appliers and other hand held or robotically controlled devices.

BRIEF DESCRIPTION OF THE DRAWINGS

Various embodiments of the presently disclosed DLU are disclosed herein with reference to the drawings, wherein.

DETAILED DESCRIPTION OF EMBODIMENTS

Embodiments of the presently disclosed DLU will now be described in detail with reference to the drawings, in which like reference numerals designate identical or corresponding elements in each of the several views.

Figure 1:
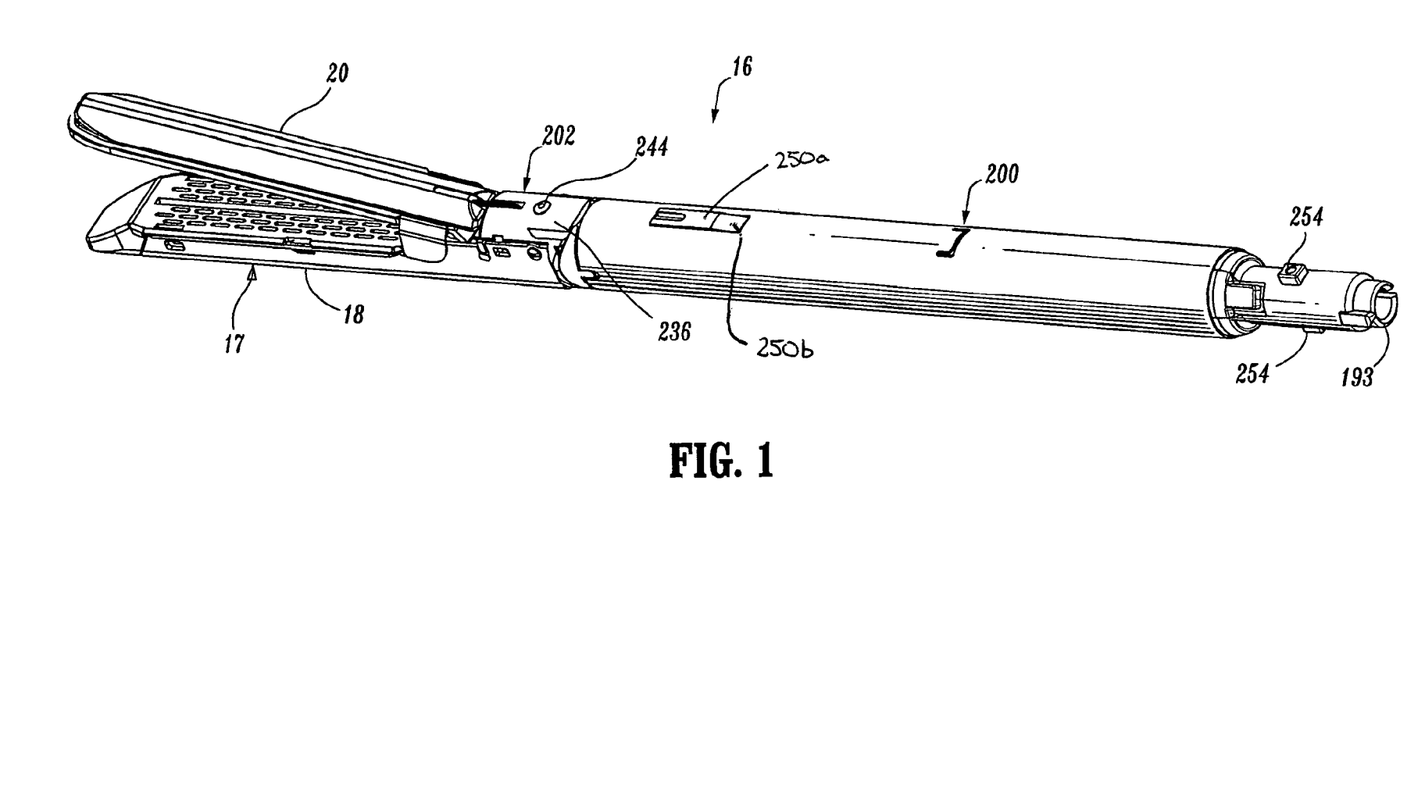
FIG. 1 is a side perspective view from the proximal end of one embodiment of the presently disclosed DLU.

Referring to FIG. 1, briefly, DLU 16 includes a tool assembly 17, a proximal body portion 200 and a mounting assembly 202. Body portion 200 has a proximal end adapted to releasably engage the distal end of a surgical instrument 500 (FIG. 11) in the manner to be discussed in detail below. Mounting assembly 202 is pivotally secured to a distal end of body portion 200 and is fixedly secured to a proximal end of tool assembly 17. Pivotal movement of mounting assembly 202 about an axis perpendicular to a longitudinal axis of body portion 200 effects articulation of tool assembly 17 between an orientation aligned with the longitudinal axis of body portion 200 and an orientation at an angle to the longitudinal axis of body portion 200.

Figure 2:
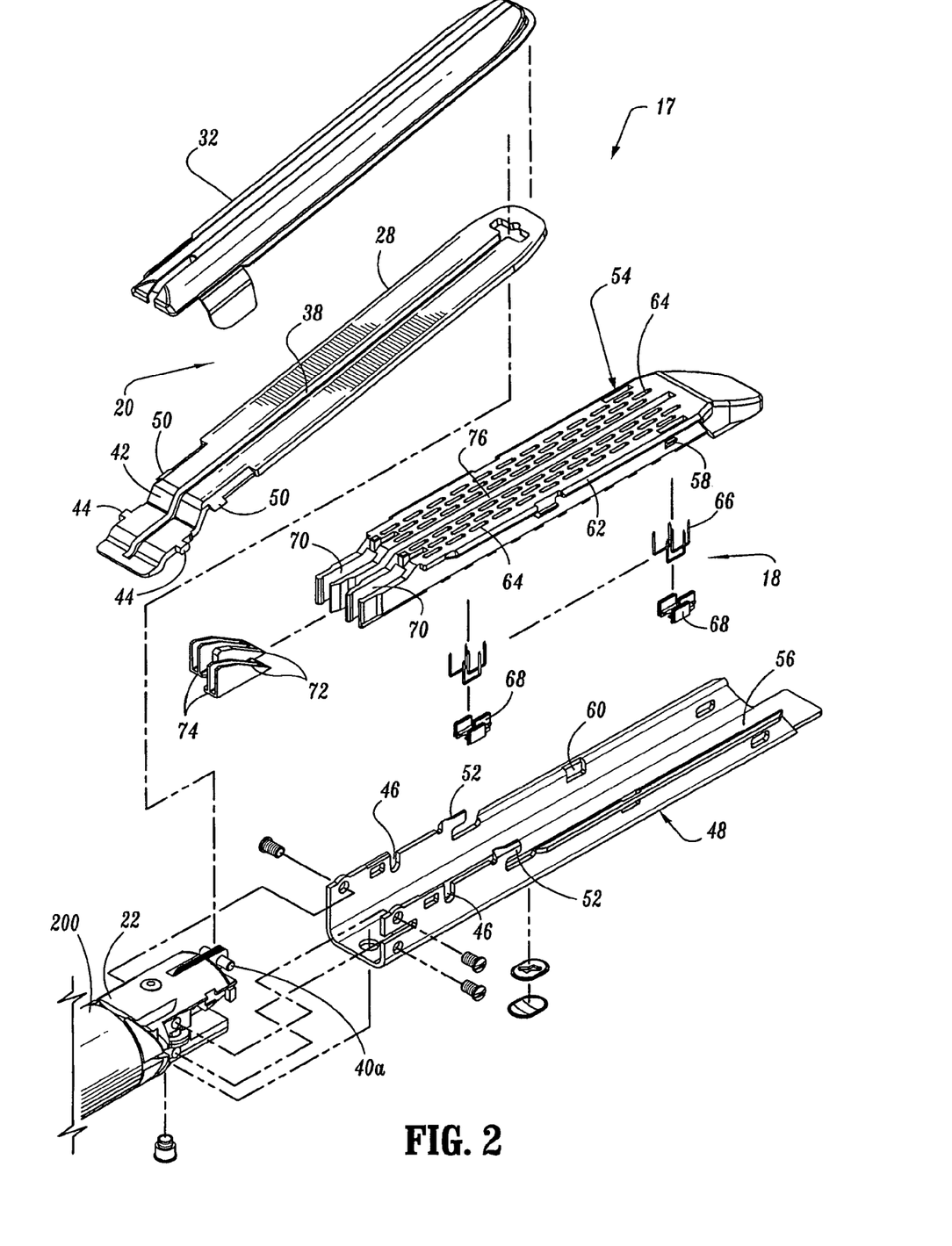
FIG. 2 is a side perspective view of the distal end of the proximal body portion, the mounting assembly and tool assembly with parts separated of the DLU shown in FIG. 1.
Figure 3:
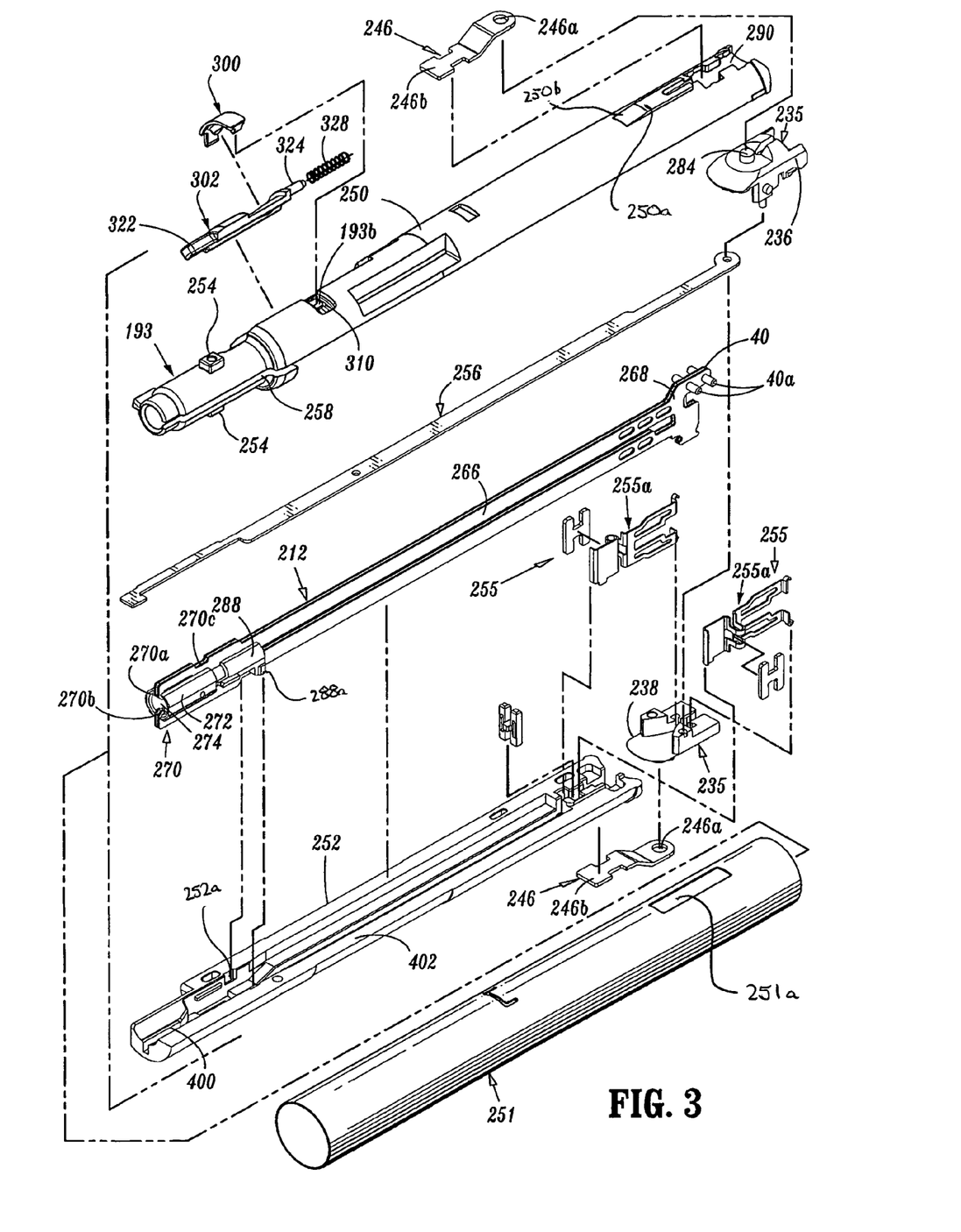
FIG. 3 is a side perspective view of the mounting assembly and the proximal body portion of the DLU shown in FIG. 1 with parts separated.
Figure 4:
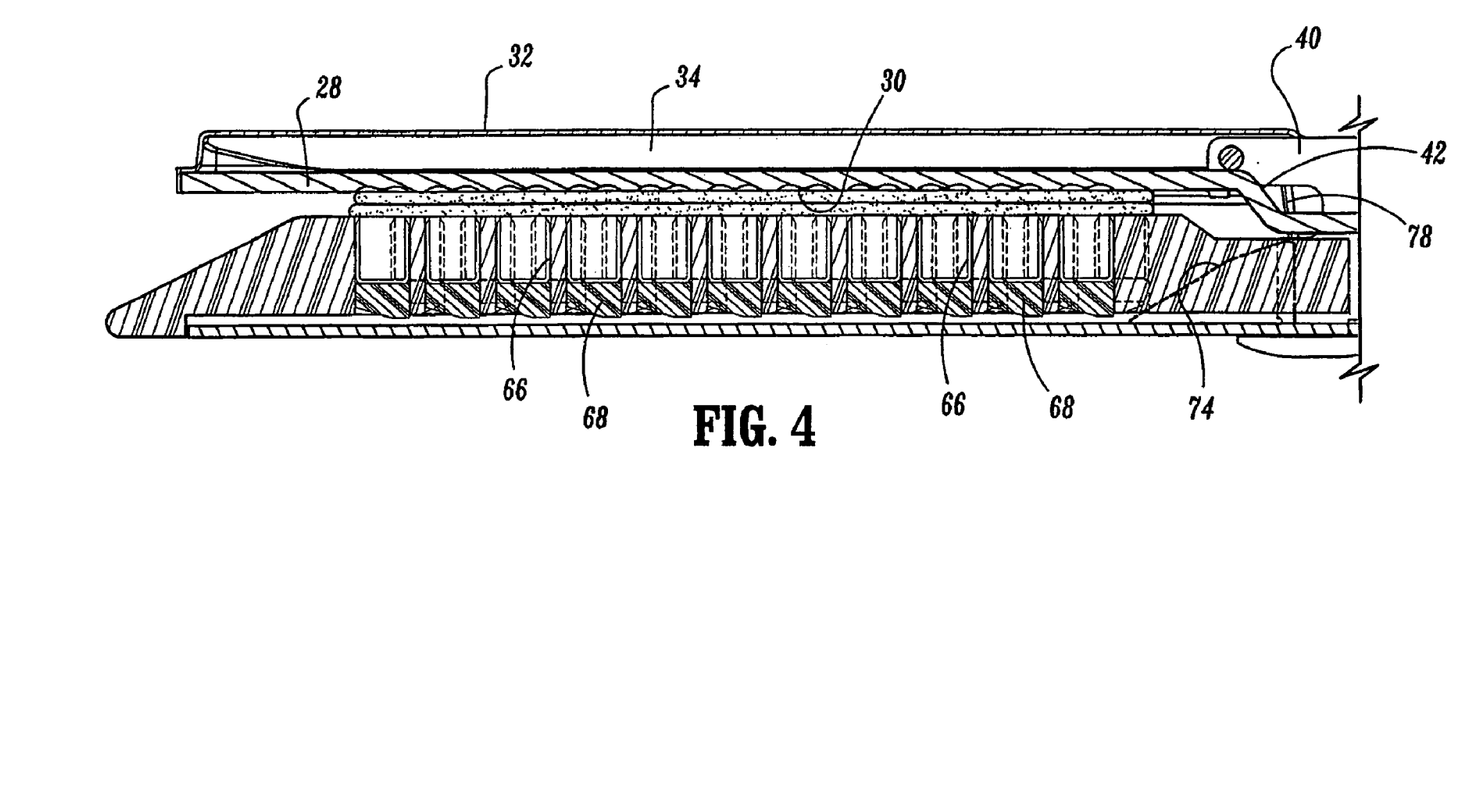
FIG. 4 is a side cross-sectional view of the tool assembly of the DLU shown in FIG. 1.

Referring also to FIGS. 2-4, tool assembly 17 includes a cartridge assembly 18 and an anvil assembly 20. Anvil assembly 20 includes an anvil portion 28 having a plurality of staple deforming concavities 30 (FIG. 4) and a cover plate 32 secured to a top surface of anvil portion 28. Cover plate 32 and anvil portion 28 define a cavity 34 (FIG. 4) therebetween which is dimensioned to receive a distal end of a drive assembly 212 (FIG. 3). Cover plate 32 encloses the distal end of drive assembly 212 to prevent pinching of tissue during actuation of DLU 16. A longitudinal slot 38 extends through anvil portion 28 to facilitate passage of a retention flange 40 of drive assembly 212. A camming surface 42 formed on anvil portion 28 is positioned to engage a pair of cam members 40a supported on retention flange 40 of drive assembly 212 to effect approximation of the anvil and cartridge assemblies. A pair of pivot members 44 formed on anvil portion 28 are positioned within slots 46 formed in a cartridge assembly carrier 48 to guide anvil portion 28 between its spaced and approximated positions. A pair of stabilizing members 50 engage a respective shoulder 52 formed on carrier 48 to prevent anvil portion 28 from sliding axially in relation to staple cartridge 54 as camming surface 42 is pivoted about pivot members 44.

Cartridge assembly 18 includes carrier 48 which defines an elongated support channel 56 which is dimensioned and configured to receive staple cartridge 54. Corresponding tabs 58 and slots 60 formed along staple cartridge 54 and elongated support channel 56, respectively, function to retain staple cartridge 54 at a fixed location within support channel 56. A pair of support struts 62 formed on staple cartridge 54 are positioned to rest on side walls of carrier 48 to further stabilize staple cartridge 54 within support channel 56.

Staple cartridge 54 includes retention slots 64 (FIG. 2) for receiving a plurality of staples or fasteners 66 and pushers 68. A plurality of laterally spaced apart longitudinal slots 70 extend through staple cartridge 54 to accommodate upstanding cam wedges 72 of an actuation sled 74 (FIG. 2). A central longitudinal slot 76 extends along substantially the length of staple cartridge 54 to facilitate passage of a knife blade 78 (FIG. 4). During operation of surgical stapler 10, drive assembly 212 abuts actuation sled 74 and pushes actuation sled 74 through longitudinal slots 70 of staple cartridge 54 to advance cam wedges 72 into sequential contact with pushers 68. Pushers 68 translate vertically along cam wedges 72 within fastener retention slots 64 and urge fasteners 66 from retention slots 64 into staple deforming cavities 30 (FIG. 4) of anvil assembly 20.

Referring to FIG. 3, mounting assembly 235 includes an upper mounting portion 236 and a lower mounting portion 238. A centrally located pivot member 284 extends from each of upper and lower mounting portions 236 and 238 through respective openings 246a formed in coupling members 246. Coupling members 246 each include an interlocking proximal portion 246b configured to be received in grooves 290 formed in the proximal end of an inner housing which is formed from upper and lower housing halves 250 and 252. Coupling members 246 retain mounting assembly 235 and upper and lower housing halves 250 and 252 in a longitudinally fixed position in relation to each other.

Upper housing half 250 and lower housing half 252 are contained within an outer sleeve 251 of body portion 200. Body portion 251 includes a cutout 251a dimensioned to receive a boss or projection 250a formed on upper housing half 250a. The positioning of projection 250a within cutout 251a prevents axial and rotational movement of upper and lower housing halves 250 and 252 within outer sleeve 251 of body portion 200. In one embodiment, boss 250a has a substantially rectangular configuration having a greater axial dimension than lateral dimension. The greater axial dimension provides increased surface area for preventing rotation of upper and lower housing halves 250 and 252 within sleeve 251. A proximal portion 250b of boss 250a is ramped. Ramped proximal portion 250b allows sleeve 251 to be slid over boss 250a as upper and lower housing halves 250 and 252 are positioned within sleeve 251. It is envisioned that boss 250a may assume other configurations, e.g., circular, square, triangular, etc., and still achieve its intended function. Further, boss 250a can be repositioned anywhere along upper housing half 250 or, in the alternative, be positioned on lower housing half 252 or partly on each housing half 250 and 252.

The proximal end or insertion tip 193 of upper housing half 250 includes engagement nubs 254 for releasably engaging the distal end of a surgical instrument in a bayonet type fashion. Housing halves 250 and 252 define a channel 400 for slidably receiving axial drive assembly 212 therein. An articulation link 256 is dimensioned to be slidably positioned within a slot 402 formed between upper and lower housing halves 250 and 252. A pair of H-block assemblies 255 are positioned adjacent the distal end of housing portion 200 and adjacent the distal end of axial drive assembly 212 to prevent outward buckling and bulging of drive assembly 212 during articulation and firing of surgical stapling apparatus 10. Each H-block assembly 255 includes a flexible body 255a which includes a proximal end fixedly secured to body portion 200 and a distal end fixedly secured to mounting assembly 235.

A retention member 288 is supported on engagement section 270 of axial drive assembly 212. Retention member 288 includes a pair of fingers 288a which are releasably positioned within slots or recesses 252a formed in lower housing half 252. In operation, when SULU 16 is attached to a surgical instrument and axial drive assembly 212 is actuated by applying a predetermined force to an actuation member 516 of the surgical instrument 500 (FIG. 11), axial drive assembly 212 is advanced distally to move drive assembly 212 and retention member 288 distally. As retention member 288 is advanced distally, fingers 288a are forced from recesses 252a to provide an audible and tactile indication that the surgical instrument has been actuated. Retention member 288 is designed to prevent inadvertent partial actuation of DLU 16, such as during shipping, by maintaining axial drive assembly 212 at a fixed position within DLU 16 until a predetermined axial force has been applied to axial drive assembly 212.

Axial drive assembly 212 includes an elongated drive beam 266 including a distal working head 268 and a proximal engagement section 270. In one embodiment, drive beam 266 is constructed from multiple stacked sheets of material. Engagement section 270 includes a pair of resilient engagement fingers 270a and 270b which mountingly engage a pair of corresponding retention slots formed in drive member 272. Drive member 272 includes a proximal porthole 274 configured to receive distal end of a control rod 520 (FIG. 11) of a surgical instrument when the proximal end of DLU 16 is engaged with the body portion 412 of a surgical instrument 500.

Referring also to FIGS. 5-10, DLU 16 further includes a locking mechanism including a locking member 300 and a locking member actuator 302. Locking member 300 (FIG. 6) is rotatably supported within a longitudinal or axial slot 310 (FIG. 7) formed in a proximal portion of upper housing half 250 of body portion 200 of DLU 16. Locking member 300 is movable from a first position (FIGS. 7 and 8), in which locking member 300 maintains drive assembly 212 in a pre-fired position, to a second position (FIGS. 9 and 10), in which drive assembly 212 is free to move axially.

Figure 6:
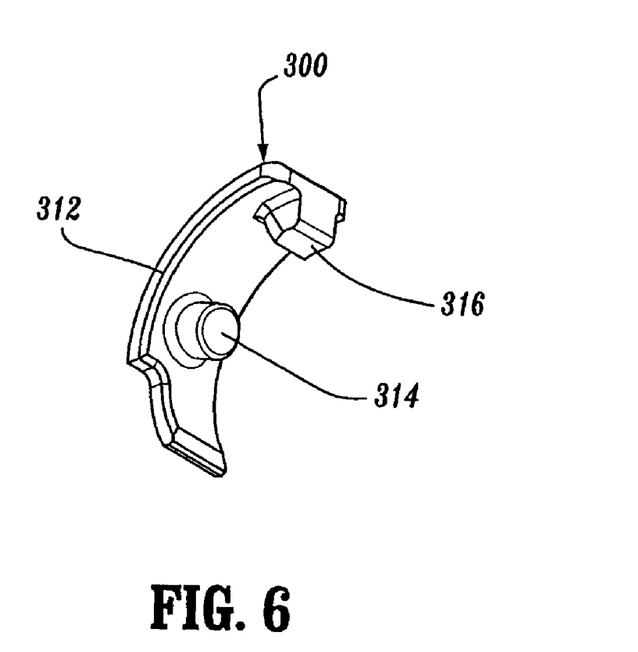
FIG. 6 is a bottom perspective view of the locking member of the locking mechanism of the proximal body portion shown in FIG. 3.

As illustrated in FIG. 6, locking member 300 includes semi-cylindrical body 312 which is slidably positioned within transverse slot 310 formed in upper housing half 250 of body portion 200. Body 312 includes a radially inwardly extending cam member 314 and a radially inwardly extending finger 316. Finger 316 is dimensioned to be slidably received within a notch or slot 270c (FIG. 3) formed in drive assembly 212. Engagement of finger 316 in notch 270c of drive assembly 212 prevents drive assembly 212 from moving linearly within body portion 200 and, thus, prevents actuation of DLU 16.

Figure 5:
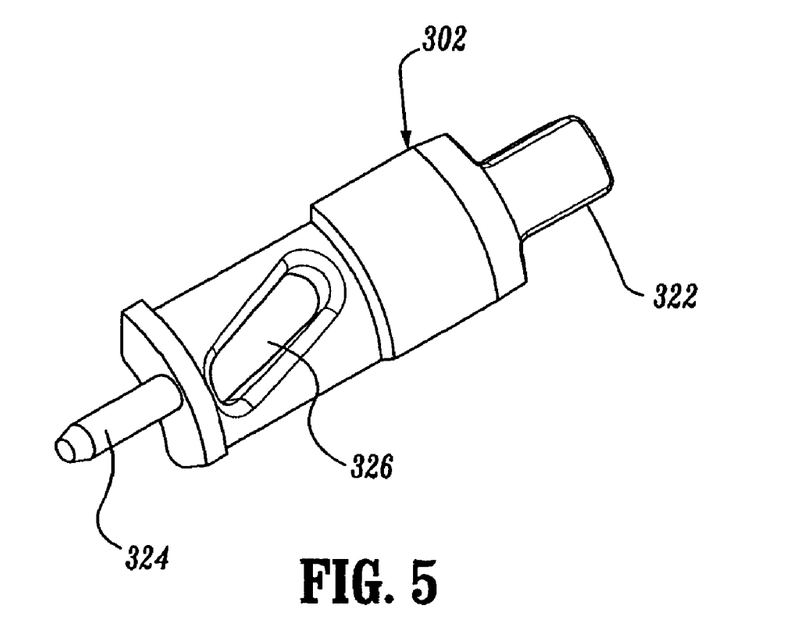
FIG. 5 is a top perspective view of the lock member actuator of the locking mechanism of the proximal body portion shown in FIG. 3.
Figure 7:
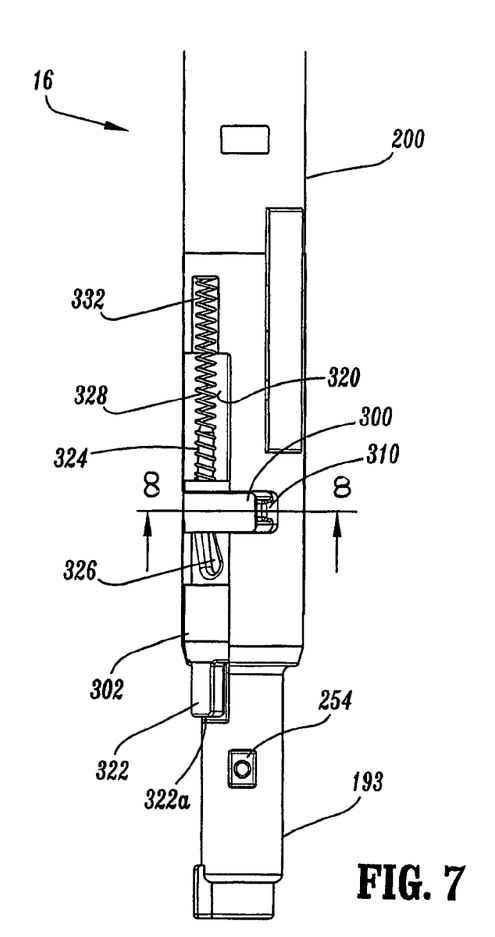
FIG. 7 is a top view of the proximal end of the proximal body portion of the DLU shown in FIG. 1 with the locking mechanism in its locked position.
Figure 8:
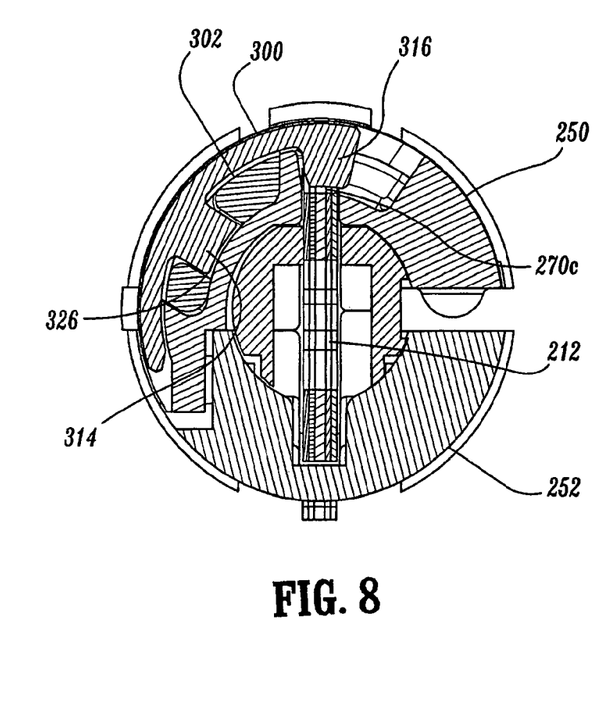
FIG. 8 is a cross-sectional view taken along section lines 8-8 of FIG. 7.
Figure 9:
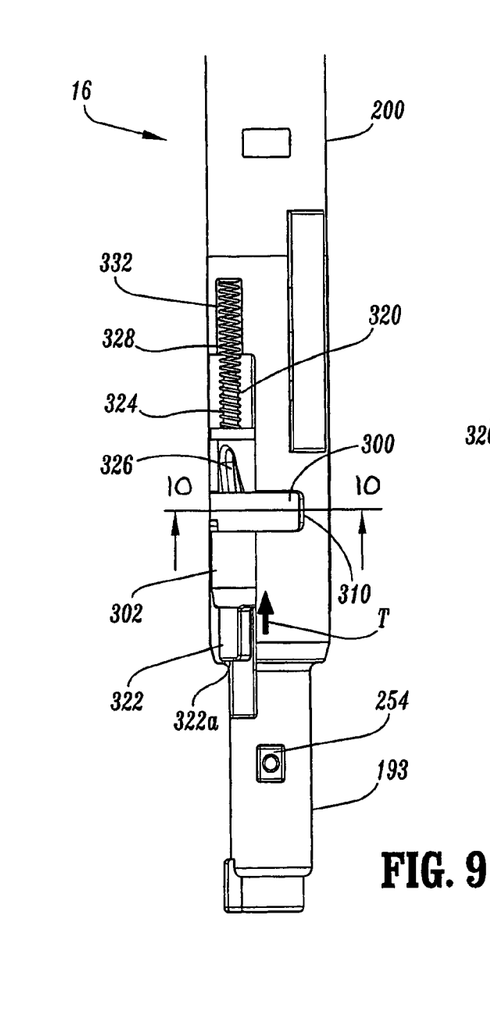
FIG. 9 is a top view of the proximal end of the proximal body portion of the DLU shown in FIG. 1 with the locking mechanism in its unlocked position.
Figure 10:
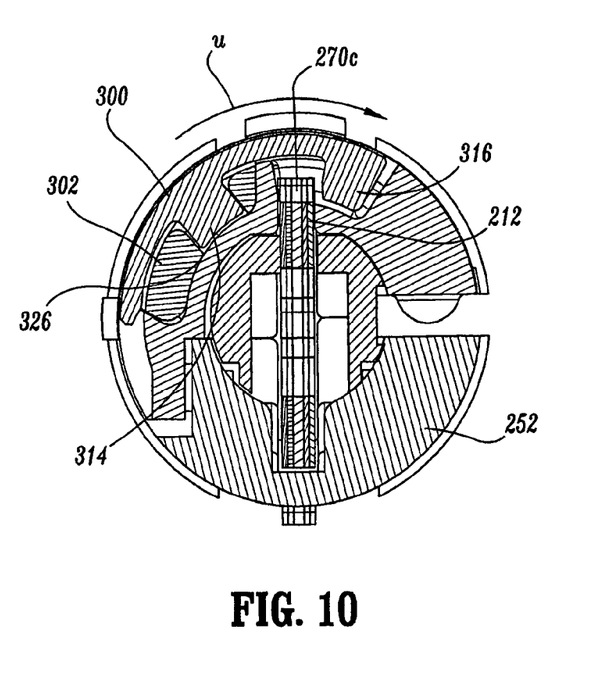
FIG. 10 is a cross-sectional view taken along section lines 10-10 of FIG. 9.

Referring to FIGS. 3, 5 and 7, a locking member actuator 302 is slidably positioned within a axial slot 320 (FIG. 7) formed in upper housing half 250 of body portion 200 of DLU 16. Actuator 302 includes a proximal abutment member 322, a distal spring guide 324, and a central cam slot 326. Axial slot 320 intersects transverse slot 310 such that cam member 314 of locking member 300 is slidably positioned within cam slot 326 of locking member actuator 302. A biasing member or spring 328 (FIG. 7) is positioned about spring guide 324 between a distal surface 330 of actuator 302 and a wall 332 (FIG. 7) defining the distal end of axial slot 320. Spring 328 urges actuator 302 to its retracted position within axial slot 320. In its retracted position, abutment member 322 is positioned on and extends radially outwardly of the proximal end of DLU 16 adjacent insertion tip 193 of proximal body portion 200 and cam slot 326 is positioned to locate cam member 314 such that finger 316 of lock member 300 is positioned within notch 270c of drive assembly 212.

Figure 11:
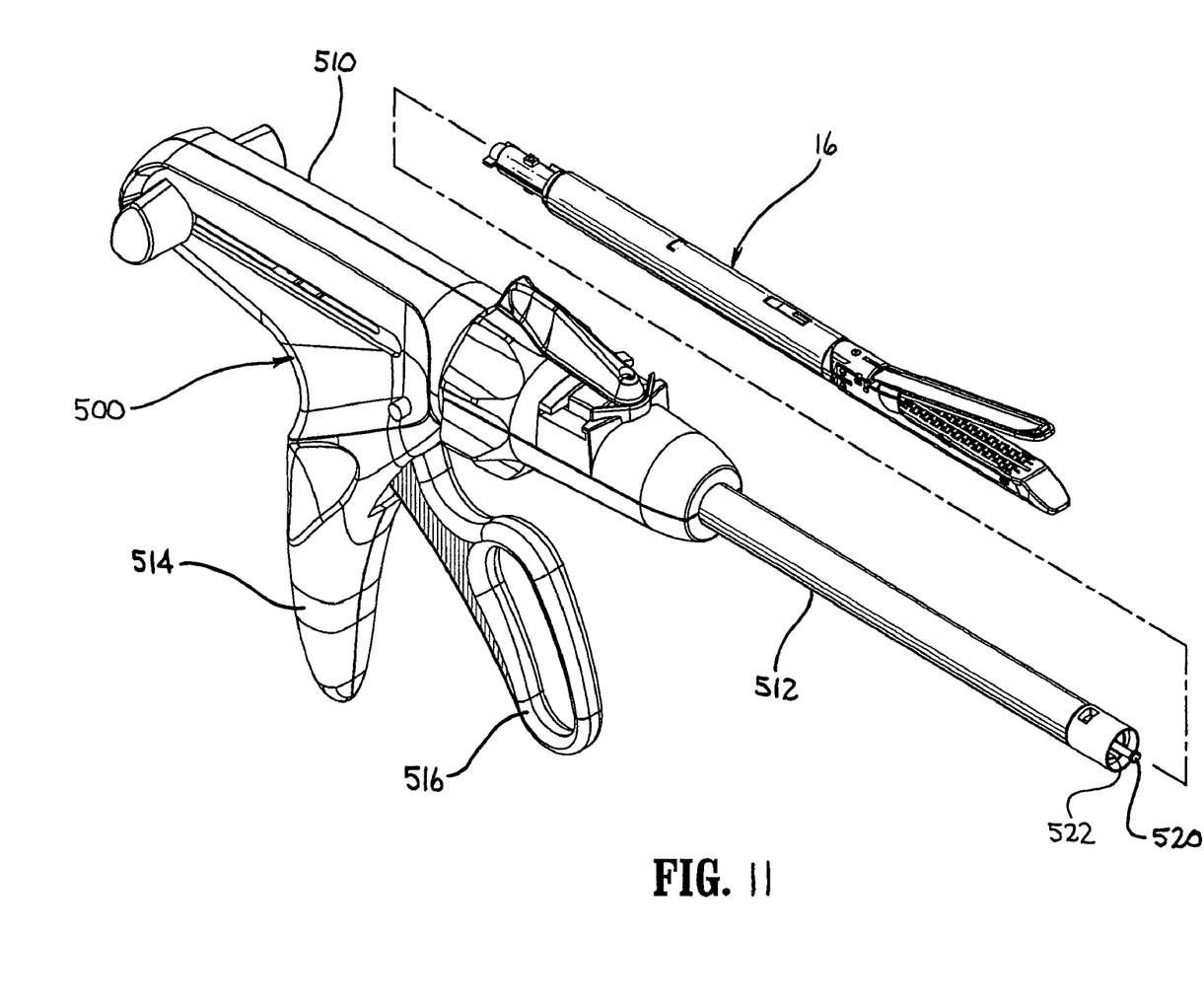
FIG. 11 is a side perspective view of the DLU shown in FIG. 1 and a surgical instrument prior to attachment of the DLU to the surgical instrument.
Figure 12:
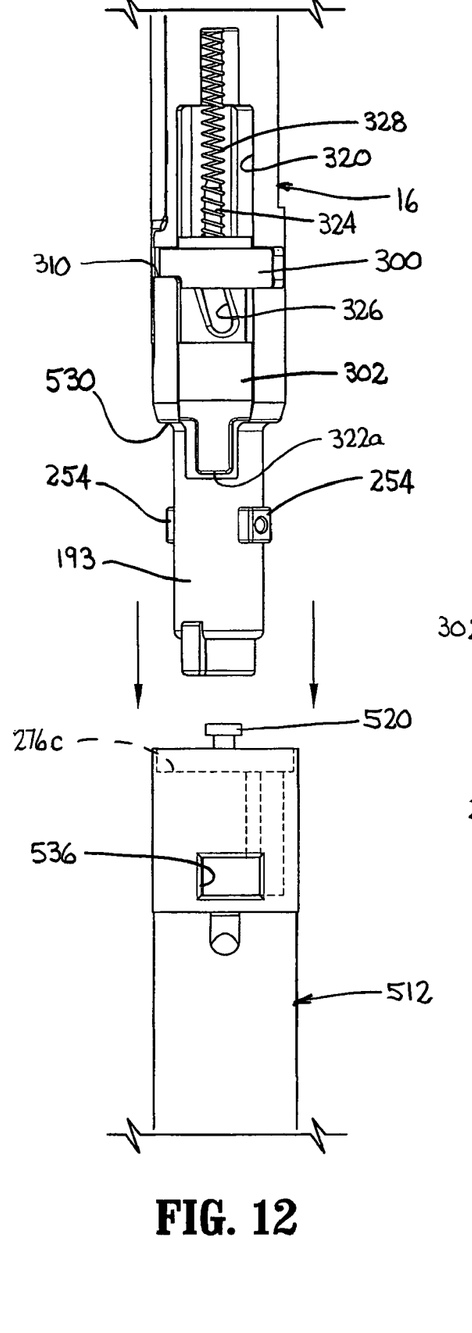
FIG. 12 is a top view of the proximal end of the DLU shown in FIG. 1 prior to attachment to the distal end of a surgical instrument.
Figure 13:
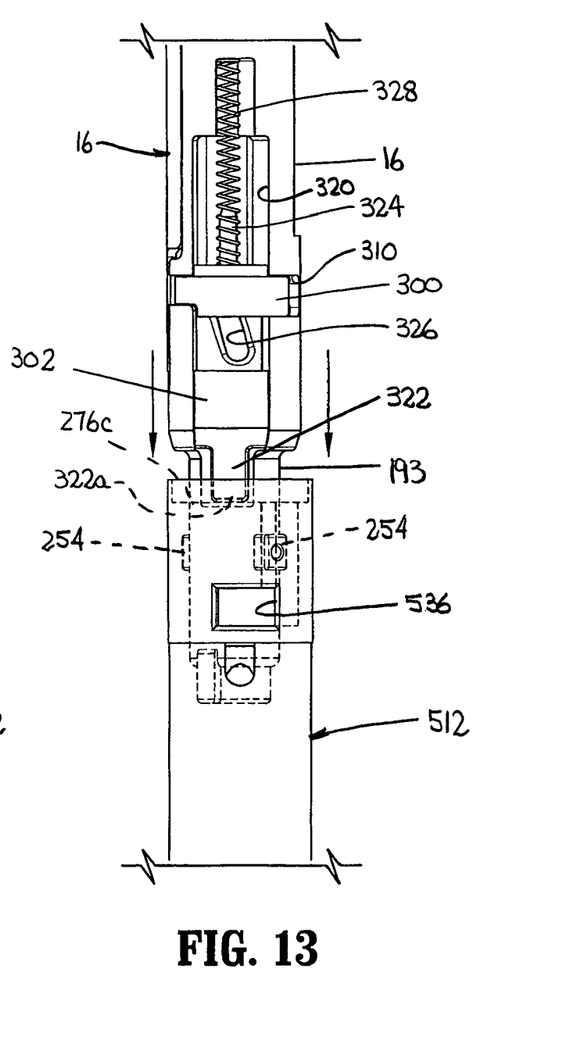
FIG. 13 is a top view of the proximal end of the DLU shown in FIG. 11 as the DLU is advanced linearly into the distal end a surgical instrument.

FIGS. 11-16 illustrate DLU 16 and surgical instrument 500 prior to and during attachment of DLU 16 to surgical instrument 500. Referring to FIGS. 11-13, surgical instrument 500 includes a handle portion 510 and body portion 512. Handle portion 510 includes a stationary handle 514 and a movable handle 516. Movable handle 516 is movable in relation to stationary handle 514 to advance a control rod 520 which projects from a distal end of body portion 512. Surgical instrument 500 may be the stapling instrument disclosed in U.S. Pat. No. 6,330,965 which is incorporated herein in its entirety by reference.

Figure 14:
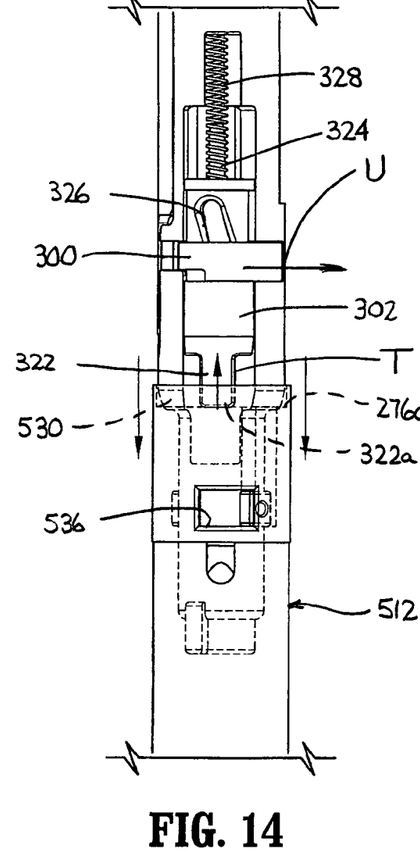
FIG. 14 is a top view of the proximal end of the DLU shown in FIG. 12 after the DLU has been advanced linearly in relation to the distal end of a surgical instrument but prior to rotatably locking the DLU to the surgical instrument.

Prior to attachment of DLU 16 onto surgical instrument 500, spring 328 urges actuator 302 to its retracted position to move lock member 300 to its locked position as discussed above. When insertion tip 193 DLU 16 is linearly inserted into the open end 522 (FIG. 11) of the body portion 512 (FIG. 13) of a surgical instrument 500, nubs 254 move linearly through slots (not shown) formed in open end 522 of body portion 512. As nubs 254 pass through the slots, the proximal end 322a of abutment member 322, which is angularly offset from nubs 254, abuts a wall 276c defining the slots for receiving nubs 254. As DLU 16 is moved further into body portion 512, locking member actuator 302 is moved from its retracted position to its advanced position in the direction indicated by arrow "T" in FIG. 14. As actuator 302 is moved to its advanced position, lock member 300 is cammed in the direction indicated by arrow "U" in FIG. 14 from its locked position (FIG. 8) engaged with drive assembly 212 to its unlocked position (FIG. 10) to move finger 316 from notch 270c. The locking mechanism including locking member 300 and locking member actuator 302 prevents accidental or inadvertent advancement or manipulation of the drive member of DLU 16 such as during loading of DLU 16 onto a surgical instrument 500.

Figure 15:
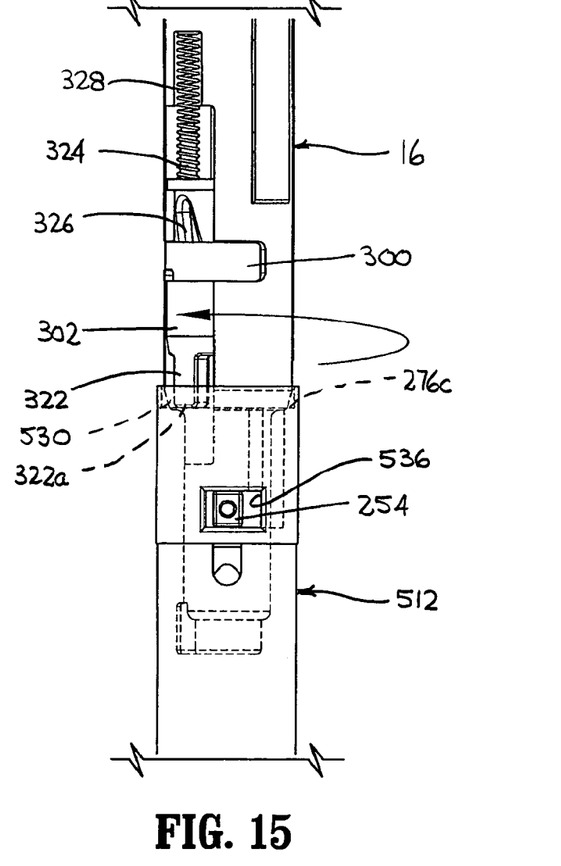
FIG. 15 is a top view of the proximal end of the DLU shown in FIG. 13 after the DLU has been advanced linearly in relation to and rotatably locked onto the surgical instrument.
Figure 16:
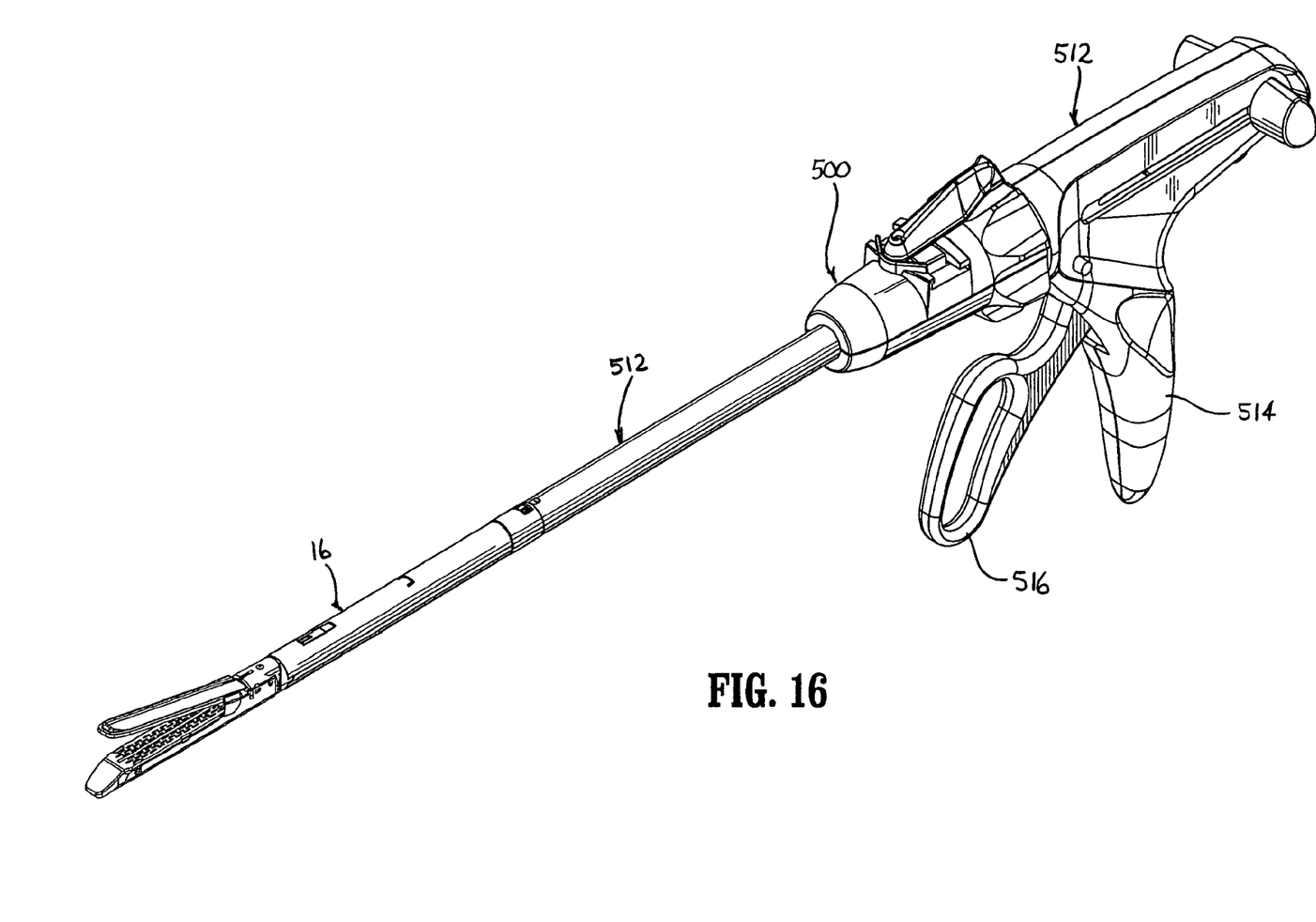
FIG. 16 is a side perspective view from the distal end of the surgical instrument and DLU shown in FIG. 11 attached together.

When DLU 16 has been moved linearly in relation to instrument 500 to a position wherein a proximal surface 530 of body portion 200 abuts inner surface 276c of body portion 512 (FIG. 15), DLU 16 can be rotated in relation to body portion 512 in a bayonet type action to position nubs 254 within openings 536 of body portion 512 to lock DLU 16 onto body portion 512. It is envisioned that other coupling types besides bayonet couplings may be used to connect DLU 16 to instrument 500, e.g., spring detent or snap-fit couplings, friction fit couplings, interlocking members, threaded couplings etc.

It will be understood that various modifications may be made to the embodiments disclosed herein. For example, the above-described lock assembly may be incorporated into a variety of surgical instruments which include DLU's and is not limited to use on linear staplers. Further, the DLU may be configured to receive an insertion tip of surgical instrument in contrast to that disclosed. Therefore, the above description should not be construed as limiting, but merely as exemplifications of preferred embodiments. Those skilled in the art will envision other modifications within the scope and spirit of the claims appended hereto.

What is claimed is:

1. A disposable loading unit comprising:
a body portion defining a longitudinal axis and being adapted to releasably engage a surgical instrument;
a tool assembly supported on a distal end of the body portion;
a drive assembly supported within the body portion;
a locking member supported on the body portion, the locking member being movable from a first position engaged with the drive assembly to a second position disengaged from the drive assembly; and
a locking member actuator operably associated with the locking member, the locking member actuator being supported on the body portion such that linear movement of the locking member actuator from a retracted position to an advanced position in relation to the body portion effects movement of the locking member from the first position to the second position;
wherein linear movement of the locking member actuator in relation to the body portion effects transverse movement of the locking member;
wherein the locking member includes a cam member and the locking member actuator includes a cam slot, the cam member being positioned within the cam slot such that linear movement of the cam member along the longitudinal axis in relation to the cam slot effects transverse movement of the locking member.

2. A disposable loading unit according to claim 1, wherein the body portion includes a transverse slot for slidably receiving the locking member and an axial slot for slidably receiving the locking member actuator.

3. A disposable loading unit comprising:
a body portion defining a longitudinal axis and being adapted to releasably engage a surgical instrument;
a tool assembly supported on a distal end of the body portion;
a drive assembly supported within the body portion;
a locking member actuator supported on the body portion, the locking member actuator being movably supported on the body portion along an axis substantially parallel to the longitudinal axis from a retracted position wherein the drive assembly is retained in a proximal position to an advanced position wherein the drive assembly is movable to a distal position; and a locking member operably engaged with the locking member actuator, the locking member actuator being linearly movable from the retracted position to the advanced position to effect movement of the locking member from a first position engaged with the drive assembly to a second position disengaged from the drive assembly wherein movement of the locking member actuator from the retracted position to the advanced position effects transverse movement of the locking member in relation to the longitudinal axis of the body portion; and
wherein the locking member includes a cam member and the locking member actuator includes a cam slot, the cam member being positioned within the cam slot such that linear movement of the cam member in relation to the cam slot effects transverse movement of the locking member.

4. A disposable loading unit according to claim 3, wherein the body portion includes a transverse slot for slidably receiving the locking member and an axial slot for slidably receiving the locking member actuator.

* * * * *